(12) United States Patent
Chen et al.

(10) Patent No.: US 9,759,711 B2
(45) Date of Patent: Sep. 12, 2017

(54) NANOPORE ARRAYS

(71) Applicant: Genia Technologies, Inc., Mountain View, CA (US)

(72) Inventors: Roger J. A. Chen, Saratoga, CA (US); David J. Fullagar, Los Gatos, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/759,701

(22) Filed: Feb. 5, 2013

(65) Prior Publication Data

US 2014/0221249 A1  Aug. 7, 2014

(51) Int. Cl.
*G01N 27/327* (2006.01)
*G01N 33/487* (2006.01)

(52) U.S. Cl.
CPC .............................. *G01N 33/48721* (2013.01)

(58) Field of Classification Search
CPC ................................................ G01N 33/48721
USPC ......................................................... 506/12
See application file for complete search history.

(56) References Cited

U.S. PATENT DOCUMENTS

| | | | |
|---|---|---|---|
| 2,656,508 A | 10/1953 | Coulter | |
| 3,638,120 A | 1/1972 | Jost | |
| 4,121,192 A | 10/1978 | Wilson | |
| 4,713,347 A | 12/1987 | Mitchell et al. | |
| 4,859,945 A | 8/1989 | Stokar | |
| 5,021,692 A | 6/1991 | Hughes | |
| 5,198,543 A | 3/1993 | Blanco et al. | |
| 5,235,267 A | 8/1993 | Schoneberg et al. | |
| 5,260,663 A | 11/1993 | Blades | |
| 5,302,509 A | 4/1994 | Cheeseman | |
| 5,308,539 A | 5/1994 | Koden et al. | |
| 5,457,342 A | 10/1995 | Herbst, II | |
| 5,541,851 A | 7/1996 | Sato et al. | |
| 5,569,950 A | 10/1996 | Lewis et al. | |
| 5,576,204 A | 11/1996 | Blanco et al. | |
| 5,747,805 A | 5/1998 | Youngquist | |
| 5,756,355 A | 5/1998 | Lang et al. | |
| 5,770,367 A | 6/1998 | Southern et al. | |

(Continued)

FOREIGN PATENT DOCUMENTS

| | | |
|---|---|---|
| CN | 101421616 | 4/2009 |
| EP | 1236807 | 11/1998 |

(Continued)

OTHER PUBLICATIONS

Kim et al., Adv. Materials, 2006, 18, pp. 3149-3153.*

(Continued)

*Primary Examiner* — Karla Dines
(74) *Attorney, Agent, or Firm* — Van Pelt, Yi & James LLP

(57) ABSTRACT

A method of analyzing molecules using a nanopore array including a plurality of cells included on a chip is disclosed. Nanopores are caused to be formed in at least a portion of the plurality of the cells. A first physical measurement of the nanopores is evaluated. It is determined whether to cause the molecules to interact with the nanopores. At least a portion of the nanopores is caused to interact with the molecules. A second physical measurement of the nanopores that indicates a property of the molecules is evaluated. It is determined whether to cause the nanopores to be reformed so that the cells may be reused to interact with additional molecules.

14 Claims, 7 Drawing Sheets

(56) References Cited

U.S. PATENT DOCUMENTS

| | | |
|---|---|---|
| 5,795,782 A | 8/1998 | Church et al. |
| 5,804,386 A | 9/1998 | Ju |
| 5,814,454 A | 9/1998 | Ju |
| 5,869,244 A | 2/1999 | Martin et al. |
| 5,876,936 A | 3/1999 | Ju |
| 5,912,155 A | 6/1999 | Chatterjee et al. |
| 5,939,301 A | 8/1999 | Hughes, Jr. et al. |
| 5,952,180 A | 9/1999 | Ju |
| 5,981,733 A * | 11/1999 | Gamble et al. ............. 536/25.3 |
| 6,012,291 A | 1/2000 | Ema |
| 6,014,213 A | 1/2000 | Waterhouse et al. |
| 6,015,714 A | 1/2000 | Baldarelli et al. |
| 6,046,005 A | 4/2000 | Ju et al. |
| 6,082,115 A | 7/2000 | Strnad |
| 6,210,896 B1 | 4/2001 | Chan |
| 6,217,731 B1 | 4/2001 | Kane et al. |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,321,101 B1 | 11/2001 | Holmstrom |
| 6,362,002 B1 | 3/2002 | Denison et al. |
| 6,383,749 B2 | 5/2002 | Bochkariov et al. |
| 6,399,320 B1 | 6/2002 | Markau et al. |
| 6,399,335 B1 | 6/2002 | Kao et al. |
| 6,413,792 B1 | 7/2002 | Sauer |
| 6,485,703 B1 | 11/2002 | Cote et al. |
| 6,607,883 B1 | 8/2003 | Frey et al. |
| 6,616,895 B2 | 9/2003 | Dugas et al. |
| 6,627,748 B1 | 9/2003 | Ju et al. |
| 6,664,079 B2 | 12/2003 | Ju et al. |
| 6,673,615 B2 | 1/2004 | Denison et al. |
| 6,686,997 B1 | 2/2004 | Allen |
| 6,699,719 B2 | 3/2004 | Yamazaki et al. |
| 6,723,513 B2 | 4/2004 | Lexow |
| 6,746,594 B2 | 6/2004 | Akeson et al. |
| 6,762,048 B2 | 7/2004 | Williams |
| 6,794,177 B2 | 9/2004 | Markau et al. |
| 6,800,933 B1 | 10/2004 | Mathews et al. |
| 6,824,659 B2 | 11/2004 | Bayley et al. |
| 6,880,346 B1 | 4/2005 | Tseng et al. |
| 6,891,278 B2 | 5/2005 | Muller et al. |
| 6,916,665 B2 | 7/2005 | Bayley et al. |
| 6,952,651 B2 | 10/2005 | Su |
| 7,033,762 B2 | 4/2006 | Nelson et al. |
| 7,041,812 B2 | 5/2006 | Kumar et al. |
| 7,052,839 B2 | 5/2006 | Nelson et al. |
| 7,057,026 B2 | 6/2006 | Barnes et al. |
| 7,074,597 B2 | 7/2006 | Ju |
| 7,153,672 B1 | 12/2006 | Eickbush et al. |
| 7,189,503 B2 | 3/2007 | Akeson et al. |
| 7,223,541 B2 | 5/2007 | Fuller et al. |
| 7,229,799 B2 | 6/2007 | Williams |
| 7,238,485 B2 | 7/2007 | Akeson et al. |
| 7,244,602 B2 | 7/2007 | Frey et al. |
| 7,279,337 B2 | 10/2007 | Zhu |
| 7,321,329 B2 | 1/2008 | Tooyama et al. |
| 7,368,668 B2 | 5/2008 | Ren et al. |
| 7,405,281 B2 | 7/2008 | Xu et al. |
| 7,410,564 B2 | 8/2008 | Flory |
| 7,446,017 B2 | 11/2008 | Liu et al. |
| 7,452,698 B2 | 11/2008 | Sood et al. |
| 7,572,624 B2 | 8/2009 | Gumbrecht et al. |
| 7,622,934 B2 | 11/2009 | Hibbs et al. |
| 7,625,701 B2 | 12/2009 | Williams et al. |
| 7,626,379 B2 | 12/2009 | Peters et al. |
| 7,710,479 B2 | 5/2010 | Nitta et al. |
| 7,727,722 B2 | 6/2010 | Nelson et al. |
| 7,745,116 B2 | 6/2010 | Williams |
| 7,777,013 B2 | 8/2010 | Xu et al. |
| 7,777,505 B2 | 8/2010 | White et al. |
| 7,871,777 B2 | 1/2011 | Schneider et al. |
| 7,897,738 B2 | 3/2011 | Brandis et al. |
| 7,906,371 B2 | 3/2011 | Kim et al. |
| 7,924,335 B2 | 4/2011 | Itakura et al. |
| 7,939,259 B2 | 5/2011 | Kokoris et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,973,146 B2 | 7/2011 | Shen et al. |
| 7,989,928 B2 | 8/2011 | Liao et al. |
| 8,022,511 B2 | 9/2011 | Chiu et al. |
| 8,058,030 B2 | 11/2011 | Smith et al. |
| 8,058,031 B2 | 11/2011 | Xu et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,192,961 B2 | 6/2012 | Williams |
| 8,252,911 B2 | 8/2012 | Bjornson et al. |
| 8,257,954 B2 | 9/2012 | Clark et al. |
| 8,324,914 B2 | 12/2012 | Chen et al. |
| 8,461,854 B2 | 6/2013 | Chen et al. |
| 8,828,208 B2 | 9/2014 | Canas et al. |
| 8,962,242 B2 | 2/2015 | Chen et al. |
| 2002/0039743 A1 | 4/2002 | Hashimoto et al. |
| 2003/0027140 A1 | 2/2003 | Ju et al. |
| 2003/0054360 A1 | 3/2003 | Gold et al. |
| 2003/0080042 A1 | 5/2003 | Barth et al. |
| 2003/0101006 A1 | 5/2003 | Mansky et al. |
| 2003/0102263 A1 | 6/2003 | Lopez et al. |
| 2003/0166282 A1 | 9/2003 | Brown et al. |
| 2003/0198982 A1 | 10/2003 | Seela et al. |
| 2004/0122335 A1 | 6/2004 | Sackellares et al. |
| 2004/0144658 A1 | 7/2004 | Flory |
| 2004/0185466 A1 | 9/2004 | Ju et al. |
| 2004/0262636 A1 | 12/2004 | Yang et al. |
| 2005/0032081 A1 | 2/2005 | Ju et al. |
| 2005/0091989 A1 | 5/2005 | Leija et al. |
| 2005/0127035 A1 | 6/2005 | Ling |
| 2005/0136408 A1 | 6/2005 | Tom-Moy et al. |
| 2005/0164286 A1 | 7/2005 | O'uchi et al. |
| 2005/0186576 A1 | 8/2005 | Chan et al. |
| 2005/0208574 A1 | 9/2005 | Bayley et al. |
| 2005/0221351 A1 | 10/2005 | Ryu |
| 2005/0239134 A1 | 10/2005 | Gorenstein et al. |
| 2006/0057565 A1 | 3/2006 | Ju et al. |
| 2006/0057585 A1 | 3/2006 | McAllister |
| 2006/0105373 A1 | 5/2006 | Pourmand et al. |
| 2006/0105461 A1 | 5/2006 | Tom-Moy et al. |
| 2006/0246497 A1 | 11/2006 | Huang et al. |
| 2006/0252038 A1 | 11/2006 | Ju |
| 2006/0278992 A1 | 12/2006 | Trezza et al. |
| 2007/0173731 A1 | 7/2007 | Meka et al. |
| 2007/0190542 A1 | 8/2007 | Ling et al. |
| 2007/0191015 A1 | 8/2007 | Hwang et al. |
| 2007/0196846 A1 | 8/2007 | Hanzel et al. |
| 2007/0275387 A1 | 11/2007 | Ju |
| 2008/0101988 A1 | 5/2008 | Kang et al. |
| 2008/0108082 A1 | 5/2008 | Rank et al. |
| 2008/0171316 A1 | 7/2008 | Golovchenko et al. |
| 2008/0199932 A1 | 8/2008 | Hanzel et al. |
| 2008/0217546 A1 | 9/2008 | Steadman et al. |
| 2008/0218184 A1 | 9/2008 | White et al. |
| 2008/0254995 A1 | 10/2008 | Kim et al. |
| 2008/0286768 A1 | 11/2008 | Lexow |
| 2008/0318245 A1 | 12/2008 | Smirnov |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0087834 A1 | 4/2009 | Lexow et al. |
| 2009/0099786 A1 | 4/2009 | Oliver et al. |
| 2009/0102534 A1 | 4/2009 | Schmid et al. |
| 2009/0136958 A1 | 5/2009 | Gershow et al. |
| 2009/0167228 A1 | 7/2009 | Chung et al. |
| 2009/0167288 A1 | 7/2009 | Reid et al. |
| 2009/0215050 A1 | 8/2009 | Jenson |
| 2009/0233280 A1 | 9/2009 | Nomoto et al. |
| 2009/0269759 A1 | 10/2009 | Menchen et al. |
| 2009/0298072 A1 | 12/2009 | Ju |
| 2010/0025238 A1 | 2/2010 | Gottlieb et al. |
| 2010/0025249 A1 | 2/2010 | Polonksy et al. |
| 2010/0035260 A1 | 2/2010 | Olasagasti et al. |
| 2010/0047802 A1 | 2/2010 | Bjornson et al. |
| 2010/0072080 A1 | 3/2010 | Karhanek et al. |

(56) References Cited

U.S. PATENT DOCUMENTS

| | | |
|---|---|---|
| 2010/0075328 A1 | 3/2010 | Bjornson et al. |
| 2010/0075332 A1 | 3/2010 | Patel et al. |
| 2010/0078325 A1 | 4/2010 | Oliver |
| 2010/0078777 A1 | 4/2010 | Barth et al. |
| 2010/0084276 A1 | 4/2010 | Lindsay |
| 2010/0092952 A1 | 4/2010 | Ju et al. |
| 2010/0093555 A1 | 4/2010 | Bjornson et al. |
| 2010/0121582 A1 | 5/2010 | Pan et al. |
| 2010/0122907 A1 | 5/2010 | Standford et al. |
| 2010/0148126 A1 | 6/2010 | Guan et al. |
| 2010/0196203 A1 | 8/2010 | Sanghera et al. |
| 2010/0243449 A1 | 9/2010 | Oliver |
| 2010/0261247 A1 | 10/2010 | Hanzel et al. |
| 2010/0261287 A1 | 10/2010 | Holt et al. |
| 2010/0292101 A1 | 11/2010 | So |
| 2010/0297644 A1 | 11/2010 | Kokoris et al. |
| 2010/0301398 A1 | 12/2010 | Rothberg et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0008775 A1 | 1/2011 | Gao et al. |
| 2011/0050200 A1 | 3/2011 | Tartagni et al. |
| 2011/0053284 A1 | 3/2011 | Meller et al. |
| 2011/0059505 A1 | 3/2011 | Hanzel et al. |
| 2011/0165652 A1 | 7/2011 | Hardin et al. |
| 2011/0168968 A1 | 7/2011 | Yang et al. |
| 2011/0174625 A1 | 7/2011 | Akeson et al. |
| 2011/0189659 A1 | 8/2011 | Clark et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0218414 A1 | 9/2011 | Kamath et al. |
| 2011/0226623 A1 | 9/2011 | Timp et al. |
| 2011/0244447 A1 | 10/2011 | Korlach |
| 2011/0287414 A1 | 11/2011 | Chen et al. |
| 2012/0034602 A1 | 2/2012 | Emig et al. |
| 2012/0040343 A1 | 2/2012 | Timp et al. |
| 2012/0040869 A1 | 2/2012 | Meller et al. |
| 2012/0052188 A1 | 3/2012 | Chen et al. |
| 2012/0094278 A1 | 4/2012 | Akeson et al. |
| 2012/0094332 A1 | 4/2012 | Lee et al. |
| 2012/0115736 A1 | 5/2012 | Bjornson et al. |
| 2012/0133354 A1 | 5/2012 | Canas et al. |
| 2012/0149021 A1* | 6/2012 | Yung et al. ............... 435/6.12 |
| 2012/0160681 A1 | 6/2012 | Davis et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2012/0322679 A1 | 12/2012 | Brown et al. |
| 2013/0015068 A1 | 1/2013 | Chen et al. |
| 2013/0071837 A1* | 3/2013 | Winters-Hilt et al. ....... 435/6.11 |
| 2013/0118902 A1 | 5/2013 | Akeson et al. |
| 2013/0207205 A1 | 8/2013 | Chen |
| 2013/0244340 A1 | 9/2013 | Davis et al. |
| 2013/0263946 A1* | 10/2013 | Afzali-Ardakani et al. . 137/561 R |
| 2013/0327644 A1* | 12/2013 | Turner ................ C12Q 1/6874 204/543 |
| 2014/0034497 A1 | 2/2014 | Davis et al. |
| 2014/0296083 A1 | 10/2014 | Brown et al. |
| 2014/0329693 A1 | 11/2014 | Reid et al. |
| 2014/0346059 A1 | 11/2014 | Akeson et al. |

FOREIGN PATENT DOCUMENTS

| | | |
|---|---|---|
| EP | 1712891 | 10/2006 |
| JP | 2004205495 | 7/2004 |
| JP | 2004333485 | 11/2004 |
| JP | 2005538377 | 12/2005 |
| JP | 2008507703 | 3/2008 |
| JP | 2010502936 | 1/2010 |
| JP | 2010524436 | 7/2010 |
| JP | 2011506994 | 3/2011 |
| JP | 2012026986 | 2/2012 |
| JP | 2013512447 | 4/2013 |
| WO | 91/06678 | 5/1991 |
| WO | 93/21340 | 10/1993 |
| WO | 97/32999 | 9/1997 |
| WO | 97/46704 | 12/1997 |
| WO | 02/22883 | 3/2002 |
| WO | 02/29003 | 4/2002 |
| WO | 2004/007773 | 1/2004 |
| WO | 2004/055160 | 7/2004 |
| WO | 2005/084367 | 9/2005 |
| WO | 2006/020775 | 2/2006 |
| WO | 2007/002204 | 1/2007 |
| WO | 2007/053702 | 5/2007 |
| WO | 2007/053719 | 5/2007 |
| WO | 2007/062105 | 5/2007 |
| WO | WO-2007115694 | 10/2007 |
| WO | 2007/127327 | 11/2007 |
| WO | 2007/146158 | 12/2007 |
| WO | 2008/034602 | 3/2008 |
| WO | 2008/069973 | 6/2008 |
| WO | 2008071982 | 6/2008 |
| WO | WO-2008079169 | 7/2008 |
| WO | 2008/102120 | 8/2008 |
| WO | 2008/124107 | 10/2008 |
| WO | WO-2009005547 | 1/2009 |
| WO | 2009/051807 | 4/2009 |
| WO | WO-2009047703 | 4/2009 |
| WO | WO-2009077734 | 6/2009 |
| WO | 2009138760 | 11/2009 |
| WO | WO-2010044932 | 4/2010 |
| WO | 2010122293 | 10/2010 |
| WO | 2011/097028 | 8/2011 |
| WO | 2011103424 | 8/2011 |
| WO | 2011/106459 | 9/2011 |
| WO | 2012/009578 | 1/2012 |
| WO | 2012/088339 | 6/2012 |
| WO | 2012/088341 | 6/2012 |
| WO | 2012/121756 | 9/2012 |
| WO | 02/079519 | 10/2012 |
| WO | 2013011879 | 1/2013 |
| WO | 2013082619 | 6/2013 |

OTHER PUBLICATIONS

Reiner et al., J Am. Chem Society, Published Jan. 14, 2013, 135, pp. 3087-3094.*

Jiang et al., Nanopore-Based Technology, Methods in Molecular Biology, 2012, vol. 870, Springer Science and Business Media, Chapter 14, pp. 241-264.*

Jetha et al., Micro and Nano Technologies in Bioanalytes, Methods of Molecular Biology, Chapter 9, 2009, Humana Press, pp. 113-127.*

Schneider et al., Nature Biotechnology, Apr. 2012, vol. 30, No. 4, p. 326-328.*

Osaki et al., Analytical Chemistry, 2009, 81, pp. 9866-9870.*

Chen et al. (Nano Lett, 2004, 4(11), pp. 2293-2298).*

Molloy et al., Clin Chem Lab Med, 2005, pp. 1-11.*

Boireau, et al. Unique supramolecular assembly of a redox protein with nucleic acids onto hybrid bilayer: towards a dynamic DNA chip. Biosens Bioelectron. Feb. 15, 2005;20(8):1631-7.

Bokhari, et al. A parallel graph decomposition algorithm for DNA sequencing with nanopores. Bioinformatics. Apr. 1, 2005;21(7):889-96. Epub Nov. 11, 2004.

Buchmann, et al. Electrochemical release from gold-thiolate electrodes for controlled insertion of ion channels into bilayer membranes. Bioorg Med Chem. Mar. 15, 2004;12(6):1315-24.

Butler et al. of RNA orientation during translocation through a biological nanopore. Biophys J. Jan. 1, 2006;90(1):190-9. Epub Oct. 7, 2005.

Butler et al. Single-molecule DNA detection with an engineered MspA protein nanopore. Proc Natl Acad Sci U S A. Dec. 30, 2008;105(52):20647-52. Epub Dec. 19, 2008.

(56) References Cited

OTHER PUBLICATIONS

Butler, et al. Ionic current blockades from DNA and RNA molecules in the alphahemolysis nanopore. Biophys J. Nov. 1, 2007;93(9):3229-40. Epub Aug. 3, 2007.
Chandler, et al. Membrane surface dynamics of DNA-threaded nanopores revealed by simultaneous single-molecule optical and ensemble electrical recording. Langmuir. Feb. 3, 2004;20(3):898-905.
Churbanov, et al. Duration learning for analysis of nanopore ionic current blockades. BMC Bioinformatics. Nov. 1, 2007;8 Suppl 7:S14.
Clarke, et al. Continuous base identification for single-molucule nanpore DNA sequencing. Nat Nanotechnol. Apr. 2009;4(4):265-70. Epub Feb. 22, 2009.
Cockroft, et al. A single-molecule nanpore device detects DNA polymerase activity with single-nucleotide resolution. J am Chem Soc. Jan. 23, 2008;130(3):818-20. Epub Jan. 1, 2008.
Danelon, et al. Cell membranes suspended across nanoaperture arrays. Langmuir. Jan. 3, 2006;22(1):22-5.
Deamer, et al. Characterization of nucleic acids by nanopore analysis. Acc Chem Res. Oct. 2002;35(10):817-25.
Derrington, et al. Nanopore DNA sequencing with MspA. Proc Natl Acad Sci U S A. Sep. 14, 2010;107(37):16060-5. Epub Aug. 26, 2010.
Einstein. Investigations on the theory of Brownian movement. Dover, New York. 1956.
Ervin, et al. Simultaneous alternating and direct current readout of protein ion channel blocking events using glass nanopore membranes. Anal Chem. Mar. 15, 2008;80(6):2069-76. Epub Feb. 23, 2008.
Flusberg, et al. Direct detection of DNA methylation during single-molecule, real-time sequencing. Nat Methods. Jun. 2010;7(6):461-5. Epub May 9, 2010.
Fologea, et al. Detecting single stranded DNA with a solid state nanopore. Nano Lett. Oct. 2005;5(10):1905-9.
Fologea, et al. Slowing DNA translocation in a solid-state nanopore. Nano Lett. Sep. 2005;5(9):1734-7.
Gu, et al. Stochastic sensing of organic analytes by a pore-forming protein containing a molecular adapter. Nature. Apr. 22, 1999;398(6729):686-90.
Haas, et al. Improvement of the qualiity of self assembled bilayer lipid membrances by using a negative potential. Bioelectrochemistry. Aug. 2001;54(1):1-10.
Halverson, et al. Asymmetric blockade of anthrax protective antigen ion channel asymmetric blockade. J Biol Chem. Oct. 7, 2005;280(40):34056-62. Epub Aug. 8, 2005.
Harlepp, et al. Probing complex RNA structures by mechanical force. Eur Phys J E Soft Matter. Dec. 2003;12(4):605-15.
Heins, et al. Detecting single porphyrin molecules in a conically shaped synthetic nanopore. Nano Lett. Sep. 2005;5(9):1824-9.
Heng, et al. Stretching DNA using the electric field in a synthetic nanopore. Nano Lett. Oct. 2005;5(10):1883-8.
Heng, et al. The electromechanics of DNA in a synthetic nanopore. Biophys J. Feb. 1, 2006;90(3):1098-106. Epub Nov. 11, 2005.
Henrickson, et al. Driven DNA transport into an asymmetric nanometer-scale pore. Phys Rev Lett. Oct. 2, 2000;85(14):3057-60.
Henrickson, et al. Probing single nanometer-scale pores with polymeric molecular rulers. J Chem Phys. Apr. 7, 2010;132(13):135101. doi: 10.1063/1.3328875.
Holden, et al. Direct introduction of single protein channels and pores into lipid bilayers. J Am Chem Soc. May 11, 2005;127(18):6502-3.
Holden, et al. Direct transfer of membrane proteins from bacteria to planar bilayers for rapid screening by single-channel recording. Nat Chem Biol. Jun. 2006;2(6):314-8. Epub May 7, 2006.
Hromada, et al. Single molecule measurements within individual membrane-bound ion channels using a polymer-based bilayer lipid membrane chip. Lab Chip. Apr. 2008;8(4):602-8. Epub Feb. 29, 2008.

International Preliminary Report on Patentability issued Dec. 24, 2008 in connection with International Application No. PCT/US2007/013559.
International search report and written opinion dated Mar. 18, 2013 for PCT/US2012/063099.
International search report and written opinion dated May 3, 2012 for PCT/US2012/020827.
International search report and written opinion dated May 9, 2013 for PCT/US2013/028058.
International search report and written opinion dated May 16, 2013 for PCT Application No. US2013/022273.
International search report and written opinion dated May 16, 2013 for PCT Application No. US2013/026514.
International search report and written opinion dated Jul. 8, 2011 for PCT/US2011/064490.
International search report and written opinion dated Aug. 28, 2012 for PCT/US2011/066627.
International search report and written opinion dated Aug. 28, 2012 for PCT/US2011/066632.
International search report and written opinion dated Oct. 29, 2007 for PCT/US2007/013559.
International search report and written opinion dated Nov. 5, 2012 for PCT/US2011/064490.
International search report dated Feb. 24, 2013 for PCT/US2011/065640.
Ito, et al. Simultaneous determination of the size and surface charge of individual nanoparticles using a carbon nanotube-based Coulter counter. Anal Chem. May 15, 2003;75(10)2399-406.
Ju, et al. Cassette labeling for facile construction of energy transfer fluorescent primers. Nucleic Acids Res. Mar. 15, 1996;24(6):1144-8.
Ju, et al. Energy transfer primers: a new fluorescence labeling paradigm for DNA sequencing and analysis. Nat Med. Feb. 1996;2(2):246-9.
Ju, et al. Fluorescence energy transfer dye-labeled primers for DNA sequencing and analysis. Proc Natl Acad Sci U S A. May 9, 1995;92(10):4347-51.
Ju, et al. Four-color DNA sequencing by synthesis using cleavable fluorescent nucleotide reversible terminators. Proc Natl Acad Sci U S A. Dec. 26, 2006;103(52):19635-40. Epub Dec. 14, 2006.
Jurak, et al. Wettability and topography of phospholipid DPPC multilayers deposited by spin-coating on glass, silicon and mica slides. Langmuir. Sep. 25, 2007;23(20):10156-63. Epub Aug. 28, 2007.
Kang, et al. A storable encapsulated bilayer chip containing a single protein nanopore. J Am Chem Soc. Apr. 18, 2007;129(15):4701-5. Epub Mar. 22, 2007.
Robertson, et al. Single-molecule mass spectrometry in solution using a solitary nanopore. Proc Natl Acad Sci U S A. May 15, 2007;104(20):8207-11. Epub May 9, 2007.
Rosenblum, et al. New dye-labeled terminators for improved DNA sequencing patterns. Nucleic Acids Res. Nov. 15, 1997;25(22):4500-4.
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Rotem et al., Temperature Measurement in the Intel Core Duo Processor, 2007.
Saleh, et al. Direct detection of antibody-antigen binding using an on-chip artificial pore. Proc Natl Acad Sci U S A. Feb. 4, 2003;100(3):820-4. Epub Jan. 27, 2003.
Sanchez-Magraner, et al. Membrane insertion of *Escherichia coli* alphahemolysin is independent from membrane lysis. J Biol Chem. Mar. 3, 2006;281(9):5461-7. Epub Dec. 22, 2005.
Sauer-Budge, et al. Unzipping kinetics of double-stranded DNA in a nanopore. Phys Rev Lett. Jun. 13, 2003;90(23):238101. Epub Jun. 9, 2003.
Seo, et al. Photocleavable fluorescent nucleotides for DNA sequencing on a chip constructed by site-specific coupling chemistry. Proc Natl Acad Sci U S A. Apr. 13, 2004;101(15):5488-93. Epub Apr. 2, 2004.

(56) References Cited

OTHER PUBLICATIONS

Shim, et al. Encapsulating a single G-quadruplex aptamer in a protein nanocavity. J Phys Chem B. Jul. 17, 2008;112(28):8354-60. Epub Jun. 19, 2008.
Simon, et al. Formation and stability of a suspended biomimetic lipid bilayer on silicon submicrometer-sized pores. J Colliod Interface Sci. Apr. 15, 2007;308(2):337-43. Epub Jan. 31, 2007.
Singer et al., Nanopore Based Sequence Specific Detection of Duplex DNA for Genomic Profiling, Jan. 8, 2010, published Jan. 20, 2010, pp. 738-743.
Singh, et al. Synthesis of natural flutimide and analogous fully substituted pyrazine-2,6-diones, endonuclease inhibitors influenza of influenza virus. J Org Chem. Aug. 10, 2001;66(16):5504-16.
Smith, et al. Overstretching B-DNA: the elastic response of individual double-stranded and single-stranded DNA molecules. Science. Feb. 9, 1996;271(5250):795-9.
Stanford, et al. Transport of DNA through a single nanometer-scale pore: evolution of signal structure. IEEE Workshop on Genomic Signal Processing and Statistics. Baltimore, MD. May 26, 2004.
Stanford, et al. Using HMMs to Quantify Signals from DNA Driven Through a Nanometer-Scale Pore. IEEE Workshop on Genomic Signal Processing and Statistics. Raleigh, NC. Oct. 2002; 11-13.
Stefureac, et al. Nanopore analysis of the interaction of metal ions with prion proteins and peptides. Biochem Cell Biol. Apr. 2010;88(2):347-58.
Stefureac, et al. Transport of alpha-helical peptides through alpha-hemolysin and aerolysis pores. Biochemistry. Aug. 1, 2006;45(30):9172-9.
Stoddart, et al. Nucleobase recognition in ssDNA at the central constriction of the alpha-hemolysin pore. Nano Lett. Sep. 8, 2010;10(9):3633-7.
Stoddart, et al. Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Storm, et al. Translocation of double-strand DNA through a silicon oxide nanopore. Phys Rev E Stat Nonlin Soft Matter Phys. May 2005;71(5 Pt 1):051903. Epub May 6, 2005.
Streater, et al. Novel 3-hydroxy-2(1H)-pyridinones. Synthesis, iron(III)-chelating properties, and biological activity. J Med Chem. Jun. 1990;33(6):1749-55.
Studer, et al Formation of individual protein channels in lipid bilayers suspended in nanopores. Colloids Surf B Biointerfaces. Oct. 15, 2009;73(2):325-31. Epub Jun. 10, 2009.
Suzuki, et al. Highly reproducible method of planar lipid bilayer reconstitution in polymethyl methacrylate chip. Langmuir. Feb. 14, 2006;22(4):1937-42.
Thomson et al. Preliminary nanopore cheminformatics analysis of aptamer-target binding strength. BMC Bioinformatics. Nov. 1, 2007;8 Suppl 7:S11.
UK search and examination report dated Feb. 25, 2013 for GB Application No. 1216656.7.
UK search and examination report dated May 1, 2013 for GB Application No. 1216026.3.
U.S. Appl. No. 13/918,626.
Vercoutere, et al. Discrimination among individual Watson-Crick base pairs at the termini of single DNA hairpin molecules. Nucleic Acids Res. Feb. 15, 2003;31(4):1311-8.
Vercoutere, et al. Rapid discrimination among individual DNA hairpin molecules at single-nucleotide resolution using an ion channel. Nat Biotechnol. Mar. 2001;19(3):248-52.
Viasnoff, et al. Probing DNA base pairing energy profiles using a nanopore. Eur Biophys J. Feb. 2009;38(2):263-9. Epub Oct. 3, 2008.
Wang, et al. DNA heterogeneity and phosphorylation unveiled by single-molecule electrophoresis. Proc Natl Acad Sci U S A. Sep. 14, 2004;101(37):13472-7. Epub Sep. 1, 2004.
Wanunu, et al. DNA profiling using solid-state nanopores: detection of DNA-binding molecules. Nano Lett. Oct. 2009;9(10):3498-502.
Weng, et al. Fluid biomembranes supported on nanoporous aerogel/xerogel substrates. Langmuir. Aug. 17, 2004;20(17):7232-9.
Wilson, et al. Electronic control of DNA polymerase binding and unbinding to single DNA molecules. ACS Nan. Apr. 28, 2009;3(4):995-1003.
Wilson, et al. Feedback control of a DNA molecule tethered in a nanopore to repeatedly probe DNA-binding enzymes. Conf Proc IEEE Eng Med Biol Soc. 2008;2008:5745-8.
Winters-Hilt, et al. Nanopore-based kinetics analysis of individual antibody-channel and antibody-antigen interactions. BMC Bioinformatics. Nov. 1, 2007;8 Suppl 7:S20.
Woodside, et al. Direct measurement of the full, sequence-dependent folding landscape of a nucleic acid. Science. Nov. 10, 2006;314(5801):1001-4.
Woodside, et al. Nanomechanical measurements of the sequence-depepndent folding landscapes of single nucleic acid hairpins. Proc Natl Acad Sci U S A. Apr. 18, 2006;103(16):6190-5. Epub Apr. 10, 2006.
Wu, et al. Single-molecule detection of nitrogen mustards by covalent reaction within a protein nanopore. J Am Chem Soc. May 28, 2008;130(21):6813-9. Epub Apr. 30, 2008.
Zeineldin, et al. Using bicellar mixtures to form supported and suspended lipid bilayers on silicon chips. Langmuir. Sep. 12, 2006;22(19):8163-8.
Zwolak, et al. Electronic signature of DNA nucleotides via transverse transport. Nano Lett. Mar. 2005;5(3):421-4.
Kasianowicz, et al. Characterization of individual polynucleotide molecules using a membrane channel. Proc Natl Acad Sci U S A. Nov. 26, 1996;93(24):13770-3.
Kasianowicz, et al. Physics of DNA threading through a nanometer pore and applications to simultaneous multianalyte sesnsing. In NATO Advanced Research Workshop: Structure and dynamics of confined polymers. Kluwer Press. 2002; 141-163.
Kasianowicz, et al. Simultaneous multianalysis detection with a nanopore. Anal. Chem. 2001; 73:2268-2272.
Kasianowicz. Nanometer-scale pores: potential applications for analyte detection and DNA characterization. Dis Markers. 2002;18(4):185-91.
Kasianowicz. Nanopores: flossing with DNA. Nat Mater. Jun. 2004;3(6):355-6.
Kawano, et al. Controlling the translocation of single-stranded DNA through alphahemolysin ion channels using viscosity. Langmuir. Jan. 20, 2009;25(2):1233-7.
Krasilnikov, et al. A simple method for the determination of the pore radius of ion channels in planar lipid bilayer membranes. FEMS Microbiol Immunol. Sep. 1992;5(1-3):93-100.
Krasilnikov, et al. Single polymer molecules in a protein nanopore in the limit of a strong polymer-pore attraction. Phys Rev Lett. Jul. 7, 2006;97(1):018301. Epub Jul. 5, 2006.
Krasilnikov, et al. Sizing channels with neutral polymers. In NATO Advanced Research Workshop: Structure and dynamics of confined polymers. Kluwer Press. 2002; 97-116.
Kullman, et al. Transport of maltodextrins through maltoporin: a single-channel study. Biophys J. Feb. 2002;82(2):803-12.
Kumar, et al. PEG-labeled nucleotides and nanopore detection for single molecule DNA sequencing by synthesis. Sci Rep. 2012;2:684. Epub Sep. 21, 2012.
Kutik, et al. Dissecting membrane insertion of mitochondrial beta-barrel proteins. Cell. Mar. 21, 2008;132(6):1011-24.
Lee, et al. Enhancing the catalytic repertoire of nucleic acids: a systematic study of linker length and rigidity. Nucleic Acids Res. Apr. 1, 2001;29(7):1565-73.
Li, et al. A photocleavable fluorescent nucleotide for DNA sequencing and analysis. Proc Natl Acad Sci U S A. Jan. 21, 2003;100(2):414-9. Epub Jan. 6, 2003.
Li, et al. Ion-beam sculpting at nanometre length scales. Nature. Jul. 12, 2001;412(6843):166-9.
Linear Technology, High Efficiency Thermoelectric Cooler Controller, 2001.
Low Noise, Dual Switched Integrator, Burr-Brown Corporation, Sep. 1994.
Lundquist, et al. A new tri-orthogonal strategy for peptide cyclization. Org Lett. Sep. 19, 2002;4(19):3219-21.

(56) References Cited

OTHER PUBLICATIONS

Madampage, et al. Nanopore detection of antibody prion interactions. Anal Biochem. Jan. 1, 2010;396(1):36-41. Epub Aug. 21, 2009.
Mathe, et al. Nanopore unzipping of individual DNA hairpin molecules. Biophys J. Nov. 2004;87(5):3205-12. Epub Sep. 3, 2004.
Mathe, et al. Orientation discrimination of single-stranded DNA inside the alpha-hemolysin membrance channel. Proc Natl Acad Sci U S A. Aug. 30, 2005;102(35):12377-82. Epub Aug. 19, 2005.
Maurer, et al. Reconstitution of ion channels in agarose-supported silicon orifices. Biosens Bioelectron. May 15, 2007;22(11):2577-84. Epub Nov. 13, 2006.
McNally, et al. Optical recognition of converted DNA nucleotides for single-molecule DNA sequencing using nanopore arrays. Nano Lett. Jun. 9, 2010;10(6):2237-44.
Meller, et al. Rapid nanopore discrimination between single polynucleotide molecules. Proc Natl Acad Sci U S A. Feb. 1, 2000;97(3):1079-84.
Meller, et al. Single molecule measurements of DNA transport through a nanopore. Electrophoresis. Aug. 2002;23(16):2583-91.
Mohammad, et al. Controlling a single protein in a nanopore through electrostatic traps. J Am Chem Soc. Mar. 26, 2008;130(12)4081-8. Epub Mar. 6, 2008.
Movileanu, et al. Partitioning of a polymer into a nanoscopic protein pore obeys a simple scaling law. Proc Natl Acad Sci U S A. Aug. 28, 2001;98(18):10137-41. Epub Aug. 14, 2001.
Movileanu, et al. Partitioning of individual flexible polymers into a nanoscopic protein pore. Biophys J. Aug. 2003;85(2):897-910.
Nakane, et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Office action dated Feb. 25, 2013 for U.S. Appl. No. 13/396,522.
Office action dated Apr. 11, 2013 for U.S. Appl. No. 12/658,603.
Office action dated Apr. 26, 2012 for U.S. Appl. No. 12/658,591.
Office action dated Apr. 26, 2012 for U.S. Appl. No. 12/658,601.
Office action dated Jun. 15, 2012 for U.S. Appl. No. 12/658,604.
Office action dated Jun. 28, 2012 for U.S. Appl. No. 12/308,091.
Office action dated Aug. 3, 2012 for U.S. Appl. No. 12/658,602.
Office action dated Oct. 2, 2012 for U.S. Appl. No. 12/658,603.
Office action dated Oct. 16, 2012 for U.S. Appl. No. 12/658,601.
Office action dated Oct. 25, 2012 for U.S. Appl. No. 12/658,591.
Office action dated Nov. 26, 2011 for U.S. Appl. No. 12/308,091.
Office action dated Dec. 17, 2012 for U.S. Appl. No. 13/620,973.
Oxford Nanopore Technologies, Sensor Array Chip, Jul. 14, 2011.
Park, et al. DNA hybridization sensors based on electrochemical impedance spectroscopy as a detection tool. Sensors (Basel). 2009;9(12):9513-32. Epub Nov. 26, 2009.
Perkins, et al. Relaxation of a single DNA molecule observed by optical microscopy. Science. May 6, 1994;264(5160):822-6.
Pourmand, et al. Multiplex Pyrosequencing. Acids Res. Apr. 1, 2002;30(7):e31.
Purnell, et al. Discrimination of single base substitutions in a DNA strand immobilized in a biological nanopore. ACS Nano. Sep. 22, 2009;3(9):2533-8.
Reiner, et al. Temperature sculpting in yoctoliter volumes. J Am Chem Soc. Feb. 27, 2013;135(8):3087-94. doi: 10.1021/ja309892e. Epub Feb. 14, 2013.
Reiner, et al. Theory for polymer analysis using nanopore-based single-molecule mass spectrometry. Proc Natl Acad Sci U S A. Jul. 6, 2010;107(27):12080-5. doi: 10.1073/pnas.1002194107. Epub Jun. 21, 2010.
Rief, et al. Sequence-dependent mechanics of single DNA molecules. Nat Struct Biol. Apr. 1999;6(4):346-9.
Akeson, et al. Microsecond time-scale discrimination among polycytidylic acid, polyadenylic acid, and plolyuridylic acid as homopolymers or a s segments within single RNA molecules. Biophys J. Dec. 1999; 77(6):3227-33.
Aksimentiev, et al. Microscopic Kinetics of DNA Translocation through synthetic nanopores. Biophys J. Sep. 2004;87(3):2086-97.
Andersen. Sequencing and the single channel. Biophys J. Dec. 1999; 77(6):2899-901.
Ashkenasy, et al. Recognizing a single base in an individual DNA strand: a step toward DNA sequencing in nanopores. Angew Chem Int Ed Engl. Feb. 18, 2005;44(9):1401-4.
Atanasov, et al. Membrane on a chip: a functional tethered lipid bilayer membrane on silicon oxide surfaces. Biophys J. Sep. 2005;89(3):1780-8.
Baaken, et al. Planar microelecrode-cavity array for hig-resolution and parallel electrical recording of membrane ionic currents. Lab Chip. Jun. 2008;8(6):938-44. Epub Apr. 16, 2008.
Bai, et al. Design and synthesis of a photocleavable biotinylated nucleotide for DNA analysis by mass spectrometry. Nucleic Acids Res. Jan. 26, 2004;32(2):535-41. Print 2004.
Benner, et al. Sequence-specific detection of individual DNA polymerase complexes in real time using a nanopore. Nat Nanotechnol. Nov. 2007;2(11):718-24. Epub Oct. 28, 200.
Bezrukov, et al. Counting polymers moving through a single ion channel. Nature. Jul. 28, 1994;370(6487):279-81.
Bezrukov, et al. Dynamic partitioning of neutral polymers into a single ion channel. In NATO Advanced Research Workshop: Structure and dynamics of confined polymers. Kulwer Press. 2002; 117-130.
Bezrukov, et al. Dynamics and free energy of polymers partitioning into a nanoscale pore. Macromolecules. 1996; 29:8517-8522.
Bezrukov, et al. Neutral polymers in the nanopores of alamethicin and alpha-hemolysin. Biologicheskie Membrany 2001, 18, 451-455.
WP Thompson LTR May 28, 2013.
Mollazadeh et al. "Micropower CMOS integrated low-noise amplification, filtering, and digitization of multimodal neuropotentials." Biomedical Circuits and Systems, IEEE Transactions on 3.1 (2009): 1-10.
U.S. Appl. No. 61/170,729, filed Apr. 20, 2009.
Venkatesan et al., Nanopore Sensors for Nucleic Acid Analysis, Nature Nanotechnology, vol. 6, No. 10, pp. 615—Sep. 18, 2011.
Timp et al., Nanopore Sequencing: Electrical Measurements of the Code of Life, IEEE Transactions on Nanotechnology, vol. 9, No. 3, May 2010.
Rosenstein et al., Nanopore DNA Sensors in CMOS with On-Chip Low-Noise Preamplifiers, 2011 16th International Solid-State Sensors, Actuators and Microsystems Conference, Jun. 5-9, 2011.
Mager et al., Lipid Bilayer Deposition and Patterning via Air Bubble Collapse, Langmuir 2007, vol. 23, pp. 9369-9377.
Nakane et al., Nanopore Sensors for Nucleic Acid Analysis, Journal of Physics, Condensed Matter 15.32, Aug. 1, 2003, R1365.
Mosquera et al., Thermal Decomposition and Fractal Properties of Sputter-Deposited Platinum Oxide Thin Films, Journal of of Materials Research, pp. 829-836, Mar. 14, 2012.
Schuster et al., Self-Assembled α-Hemolysin Pores in an S-Layer-Supported Lipid Bilayer, Biochimica et Biophysica Acta 1370, (1998) 280-288.
Thei et al., Parallel Recording of Single Ion Channels: A Heterogeneous System Approach, IEEE Transactions on Nanotechnology, vol. 9, No. 3, May 2010.

* cited by examiner

NANOPORE ARRAYS

BACKGROUND OF THE INVENTION

Advances in micro-miniaturization within the semiconductor industry in recent years have enabled biotechnologists to begin packing their traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

DETAILED DESCRIPTION

Figure 1:
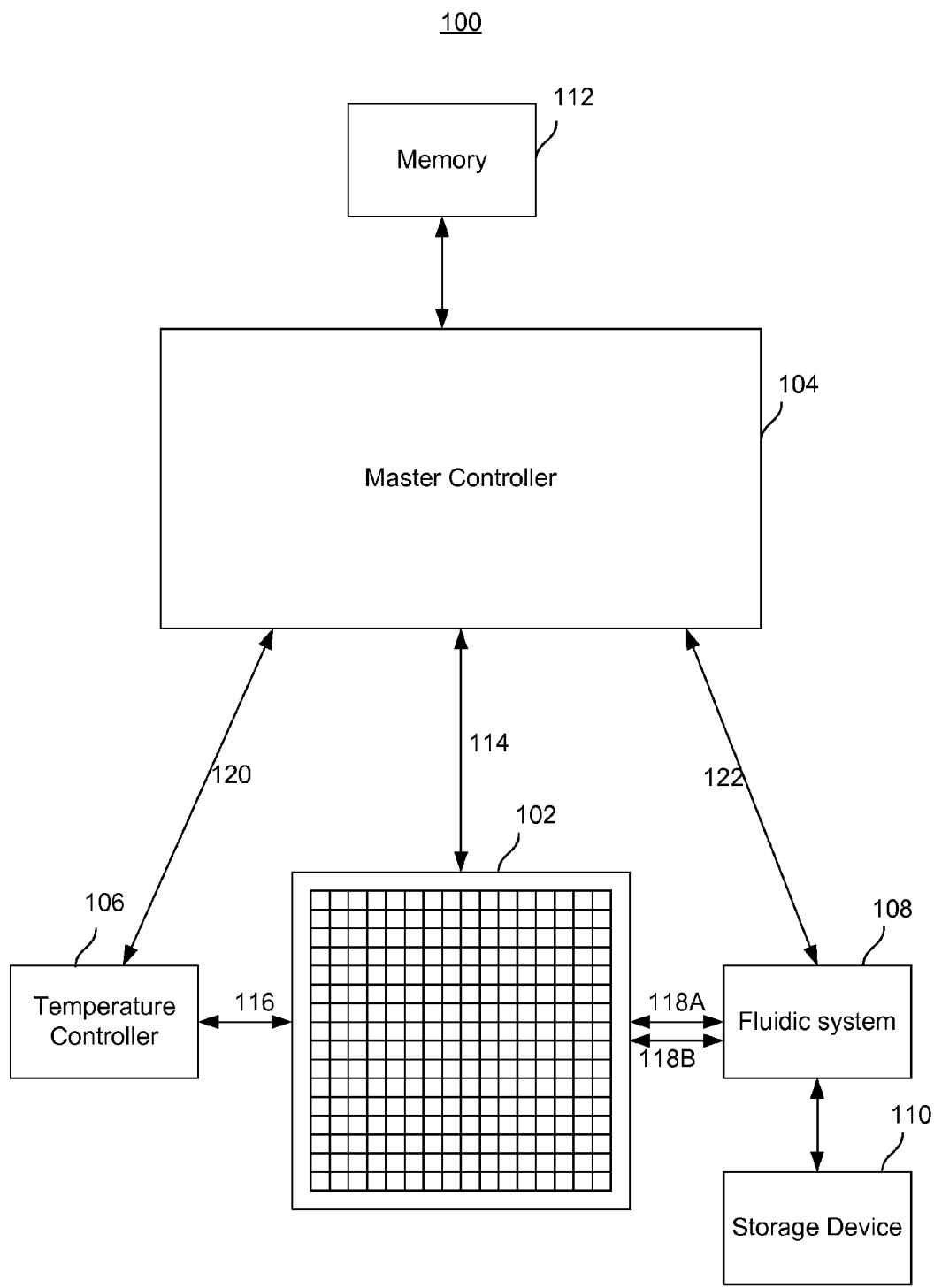
FIG. 1 is a block diagram illustrating an embodiment of a system 100 for analyzing molecules using nanopore devices.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

In various embodiments, the techniques described herein are implemented in a variety of systems or forms. In some embodiments, the techniques are implemented in hardware as an application-specific integrated circuit (ASIC) or a field-programmable gate array (FPGA). In some embodiments, a processor (e.g., an embedded one such as an ARM core) is used where the processor is provided or loaded with instructions to perform the techniques described herein. In some embodiments, the technique is implemented as a computer program product which is embodied in a computer readable storage medium and comprises computer instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Advances in micro-miniaturization within the semiconductor industry in recent years have enabled biotechnologists to begin packing their traditionally bulky sensing tools into smaller and smaller form factors, onto so-called biochips. These chips are essentially miniaturized laboratories that can perform hundreds or thousands of simultaneous biochemical reactions. Biochips enable researchers to quickly screen large numbers of biological analytes for a variety of purposes, from disease diagnosis to detection of bioterrorism agents.

Typically, a biochip includes a large array of cells. For example, a biochip for nucleotide sequencing may contain thousands or millions of single cells in an array. Each cell includes a molecular complex composed of monomers that make up an oligomeric nanopore. Each cell may further include a single strand of DNA, and anything bound to that single strand of DNA. The nanopore is a small hole in an electrically insulating membrane that can be used as a single-molecule detector. A nanopore may be formed using a biological material, such as α-hemolysin or MspA. A nanopore may be formed using a solid-state material, such as a semiconductor material. When a small voltage is applied across a molecular complex containing a nanopore, an ionic current through the molecular complex can be measured to provide information about the structure of a molecule transiting the molecular complex. In a single cell of the array, an electrical circuit may be used for controlling the electrical stimulus applied across a lipid bilayer which contains a nanopore, and for detecting and analyzing the electrical patterns, or signatures, of a molecule passing through the nanopore.

FIG. 1 is a block diagram illustrating an embodiment of a system 100 for analyzing molecules using nanopore devices. System 100 includes a nanopore array 102, a master controller 104, a temperature controller 106, a fluidic system 108, a storage device 110 for storing extracted results, and a memory 112. In some embodiments, some of the modules may be combined together as a single module, and some of the modules may be optional. In some embodiments, the cells of nanopore array 102 and the nanopore devices within the cells are individually controllable and individually addressable by other modules of system 100, including by master controller 104, temperature controller 106, and fluidic system 108. In some embodiments, performance data or other data corresponding to each of the cells may be sent from nanopore array 102 to other modules in system 100. Control, address, performance, or other data signals may be communicated between nanopore array 102 and other modules in system 100 via signal lines 114, 116, and 118A, respectively.

In some embodiments, the cells of nanopore array 102 and the nanopore devices within the cells are individually controllable and individually addressable by master controller 104. This allows master controller 104 to control each of the cells or each group of cells in nanopore array 102 such that the particular cell or particular group of cells performs different functions or transits through different states independently, without affecting the functioning or progress of other cells or other groups of cells in nanopore array 102. In one example, a mal-functioning cell in nanopore array 102 may be put in a state (e.g., disabled state) by master controller 104 such that the mal-functioning cell does not affect the functioning of other cells in nanopore array 102. For example, if a lipid bilayer fails to form in a particular cell, the cell may be disabled such that no electrical stimulus is applied to the cell; otherwise, the cell may draw a large current, which may affect the performance of other cells in nanopore array 102.

Figure 2:
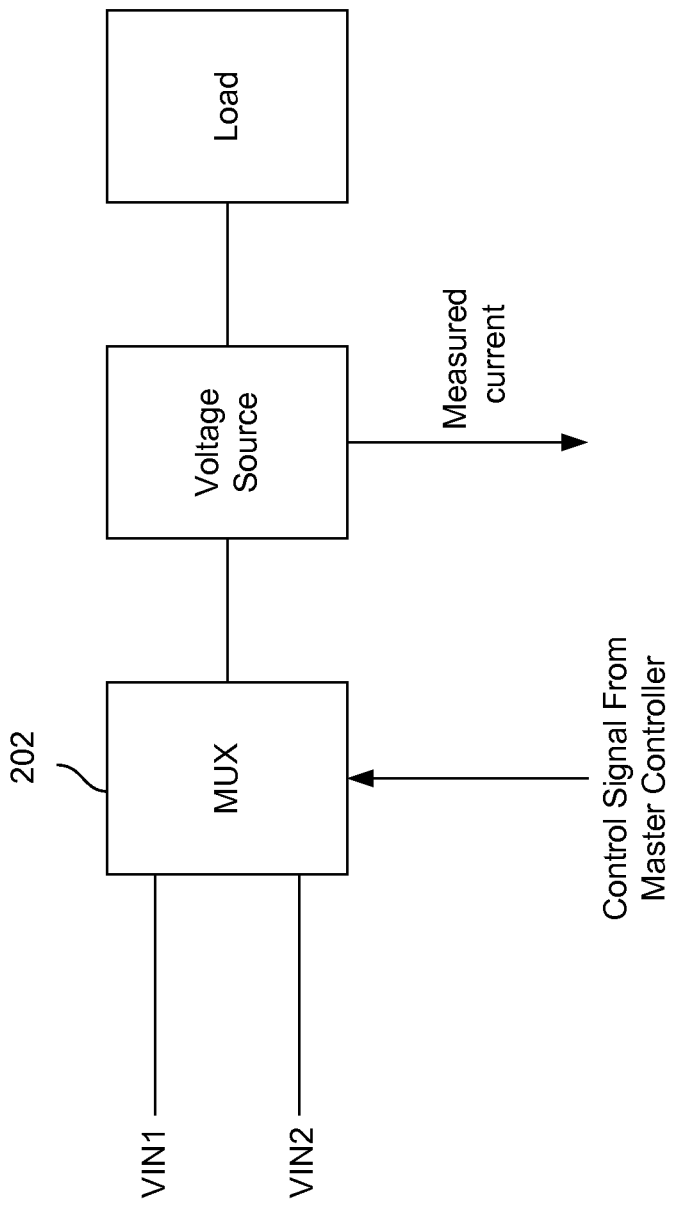
FIG. 2 is a block diagram illustrating an embodiment for applying a voltage stimulus to a cell in nanopore array 102.

In another example, master controller 104 may send control signals to nanopore array 102 such that different stimuli are applied to different cells or groups of cells. For example, a first stimulus (e.g., a voltage) is applied to a first group of cells and a second stimulus is applied to a second group of cells at time $t_1$. The first stimulus may be a stimulus corresponding to a particular state of a cell, and the second stimulus may be a stimulus corresponding to a different state of a cell. The stimulus that is applied to the first group of cells may vary over time, as the first group of cells transits from one state to another. FIG. 2 is a block diagram illustrating an embodiment for applying a voltage stimulus to a cell in nanopore array 102. As shown in FIG. 2, control signals from master controller 104 may be used as input to a multiplexer 202 to select one of two voltages that can be applied to a cell in nanopore array 102.

In some embodiments, performance or other data corresponding to each of the cells may be received by master controller 104. By monitoring the performance or other data of the cells, master controller 104 may determine any state transitions of the cells. The state information of the cells may be stored in memory 112 by master controller 104. In addition, if the overall performance of nanopore array 102 falls below a certain threshold, master controller 104 may reset and re-initialize nanopore array 102 such that any processes running on nanopore array 102 may be terminated or restarted again. In some embodiments, nanopore array 102 may also be reused multiple times. For example, nanopore array 102 may be used for analyzing different types of samples during different runs. In another example, nanopore array 102 may be reused for analyzing a single type of samples over multiple runs. In some embodiments, nanopore array 102 may be reused after the contents in nanopore array 102 have been flushed out or rinsed out by master controller 104 and fluidic system 108.

In some embodiments, the cells of nanopore array 102 are individually controllable and individually addressable by temperature controller 106 via signal line 116. Temperature or other data corresponding to a cell may be received by temperature controller 106 via signal line 116. Depending on the state or condition of a particular cell or a group of cells, different temperature stimuli may be applied to the cell or group of cells by temperature controller 106. In some embodiments, temperature controller 106 receives state information of the cells via signal line 120 and applies the appropriate temperature stimuli to the cells in nanopore array 102 at least in part based on the state information. In some embodiments, temperature controller 106 receives control signal via signal line 120 from master controller 104, and then temperature controller 106 applies the appropriate temperature stimuli to the cells in nanopore array 102 based on the received control signal.

In some embodiments, the cells of nanopore array 102 are individually controllable and individually addressable by fluidic system 108. The control and address information is communicated between nanopore array 102 and fluidic system 108 via signal lines 118A. Different contents may be delivered in and out of the individual cells of nanopore array 102 via channels 118B. The contents may be any fluids or reagents that are used for the operations within the cells of nanopore array 102, including saline solution for rinsing, samples to be analyzed by nanopore array 102, lipid bilayer forming reagent, nanopore forming reagent, gas catalyst, and the like. The contents delivered out of nanopore array 102 may be any molecules that are extracted from the samples that have been analyzed by nanopore array 102, and the extracted molecules may be further delivered to a storage device 110 by fluidic system 108. The contents may be in any form, including liquid or gas. Depending on the state or condition of a particular cell or a group of cells, different fluids may be delivered to or from the cell or group of cells by fluidic system 108. In some embodiments, fluidic system 108 receives state information of the cells via signal line 122 and delivers the appropriate fluid to or from the cells in nanopore array 102 at least in part based on the state information. In some embodiments, fluidic system 108 receives control signal via signal line 122 from master controller 104, and then fluidic system 108 delivers the appropriate fluid to or from the cells in nanopore array 102 based on the received control signal. In some embodiments, nanopore array 102 may be reused after the contents in nanopore array 102 have been flushed out or rinsed out by master controller 104 and fluidic system 108.

Nanopore array 102 includes a large array of cells. Each cell includes a nanopore device for analyzing and characterizing molecules. Within a nanopore device, a lipid bilayer is formed, and a nanopore structure is then formed on the lipid bilayer. The nanopore structure has a nanopore that is large enough for enclosing at least a portion of a molecule that is being analyzed or passing at least a portion of the molecule between the two sides of the lipid bilayer. The nanopore device also includes a sample chamber for holding a solution of the analyzed molecules. The solution may be provided over the lipid bilayer for introducing the analyzed molecules for characterization. The nanopore device further includes means for providing electrical stimulus, sensing electrical characteristics, detecting and processing signal of the nanopore device.

Figure 3:
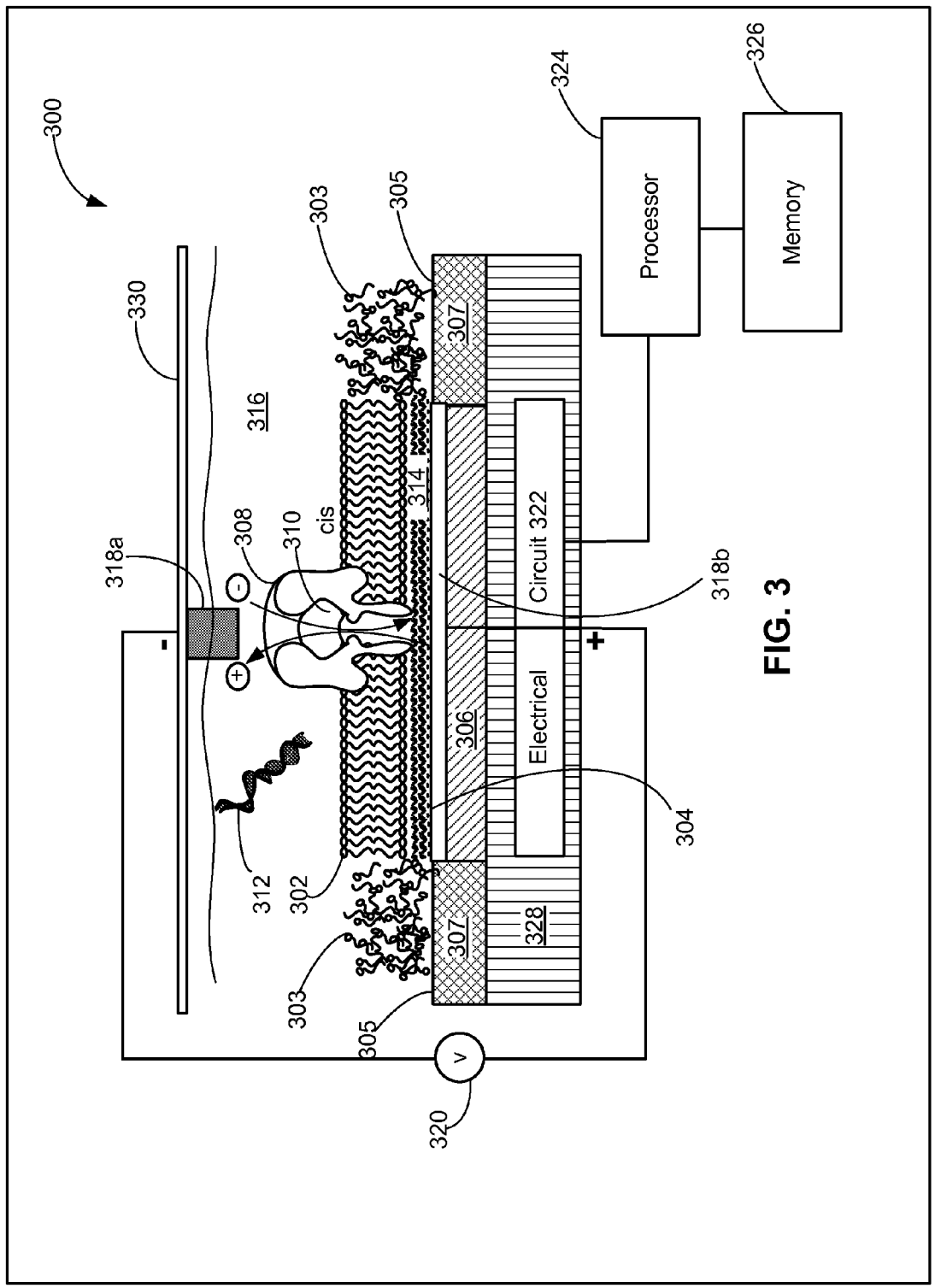
FIG. 3 is a diagram illustrating an embodiment of a nanopore device 300 within a cell of nanopore array 102.

FIG. 3 is a diagram illustrating an embodiment of a nanopore device 300 within a cell of nanopore array 102. Nanopore device 300 includes a lipid bilayer 302 formed on a lipid bilayer compatible surface 304 of a conductive solid substrate 306. Lipid bilayer compatible surface 304 may be isolated by lipid bilayer incompatible surfaces 305, and conductive solid substrate 306 may be electrically isolated by insulating materials 307. Lipid bilayer 302 may be surrounded by an amorphous lipid 303 formed on lipid bilayer incompatible surfaces 305.

In some embodiments, lipid bilayer 302 is embedded with a single nanopore structure 308 having a nanopore 310 large enough for passing at least a portion of a molecule 312 being characterized and/or small ions (e.g., $Na^+$, $K^+$, $Ca^{2+}$, $Cl^-$) between the two sides of lipid bilayer 302. A layer of water molecules 314 (also referred to as an aqueous film 314) may be adsorbed on lipid bilayer compatible surface 304 and sandwiched between lipid bilayer 302 and lipid bilayer compatible surface 304. Aqueous film 314 adsorbed on the hydrophilic lipid bilayer compatible surface 304 may promote the ordering of lipid molecules and facilitate the formation of lipid bilayer 302 on lipid bilayer compatible surface 304.

A sample chamber 316 may be provided over lipid bilayer 302 for introducing a sample for characterization. The sample may be a solution of molecule 312 that is being characterized. The solution may be an aqueous solution containing electrolytes and buffered to an optimum ion concentration and maintained at an optimum pH to keep nanopore 310 open. In some embodiments, sample chamber 316 receives the sample from fluidic system 108. The sample may also be flushed out of nanopore device 300 by fluidic system 108 after the characterization of the sample has been performed. Sample chamber 316 may also be rinsed with saline solution by fluidic system 108 such that nanopore device 300 may be reused again.

Nanopore device 300 includes a pair of electrodes 318 (including a negative node 318a and a positive node 318b) coupled to a variable voltage source 320 for providing electrical stimulus (e.g., voltage bias) across the lipid bilayer 302 and for sensing the electrical characteristics of the lipid bilayer 302 (e.g., resistance, capacitance, and ionic current flow). The surface of the negative positive electrode 318b is or forms a part of the lipid bilayer compatible surface 304. The conductive solid substrate 306 may be coupled to or forms a part of one of the electrodes 318. Nanopore device 300 may also include an electrical circuit 322 for controlling electrical stimulation and for processing the signal detected. In some embodiments, the variable voltage source 320 is included as a part of the electrical circuit 322. The electrical circuitry 322 may include amplifiers, integrators, noise filters, feedback control logic, and/or various other components. In some embodiments, the electrical circuitry 322 may be an integrated electrical circuitry integrated within a silicon substrate 328 and may be further coupled to a computer processor 324 coupled to a memory 326. For example, computer processor 324 may be a portion of master controller 104, and memory 326 may be memory 112 that is coupled to master controller 104. Master controller 104 may control the various components of nanopore device 300 via electrical circuit 322. Master controller 104 may also receive data collected by nanopore device 300 via electrical circuit 322.

The lipid bilayer compatible surface 304 can be formed from various materials that are suitable for ion transduction and gas formation to facilitate lipid bilayer formation. In some embodiments, conductive or semi-conductive hydrophilic materials as opposed to insulating hydrophilic materials are preferred because they may allow better detection of a change in the lipid bilayer electrical characteristics. Example materials include Ag—AgCl, Ag—Au alloy, Ag—Pt alloy, or doped silicon or other semiconductor materials.

The lipid bilayer incompatible surface 305 can be formed from various materials that are not suitable for lipid bilayer formation and they are typically hydrophobic. In some embodiments, a non-conductive hydrophobic material is preferred, since it electrically insulates the lipid bilayer regions in addition to separating the lipid bilayer regions from each other. Example lipid bilayer incompatible materials include silicon nitride (e.g., $Si_3N_4$) and Teflon.

In one particular example, nanopore device 300 of FIG. 3 is a alpha hemolysin (αHL) nanopore device having a single αHL protein embedded in a diphytanoylphosphatidylcholine (DPhPC) lipid bilayer 302 formed over a lipid bilayer compatible silver-gold alloy surface 304 coated on a copper material 306. The lipid bilayer compatible silver-gold alloy surface 304 is isolated by lipid bilayer incompatible silicon nitride surfaces 305, and the copper material 306 is electrically insulated by silicon nitride materials 307. The copper 306 is coupled to electrical circuitry 322 that is integrated in a silicon substrate 328. A silver-silver chloride electrode placed on-chip or extending down from a cover plate contacts an aqueous solution containing dsDNA molecules.

The αHL nanopore is an assembly of seven individual peptides. The entrance or vestible of the αHL nanopore is approximately 26 Å in diameter, which is wide enough to accommodate a portion of a dsDNA molecule. From the vestible, the αHL nanopore first widens and then narrows to a barrel having a diameter of approximately 15 Å, which is wide enough to allow a single ssDNA molecule to pass through but not wide enough to allow a dsDNA molecule to pass through. At a given time, approximately 1-20 DNA bases can occupy the barrel of the αHL nanopore.

In addition to DPhPC, the lipid bilayer of the nanopore device can be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methylester (DOPME), diphytanoylphosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the αHL nanopore shown above, the nanopore may be one of various other types of nanopores; examples include γ-hemolysin, leukocidin, melittin, and various other naturally occurring, modified natural, and synthetic nanopores. A suitable nanopore may be selected based on various characteristics of the analyte molecule, such as the size of the analyte molecule in relation to the pore size of the nanopore. For example, the αHL nanopore is a nanopore that has a restrictive pore size of approximately 15 Å. It is suitable for analyzing DNA molecules since it allows a single strand DNA (ssDNA) to pass through while restricting a double strand DNA (dsDNA).

Figure 4A:
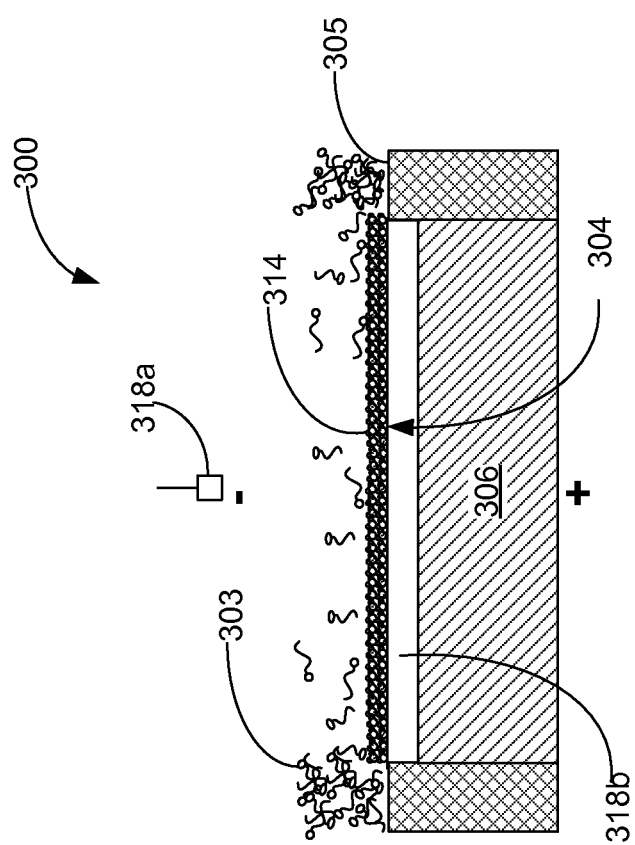
FIG. 4A is a diagram illustrating that nanopore device 300 is in a state in which a lipid bilayer has not yet been formed.
Figure 4B:
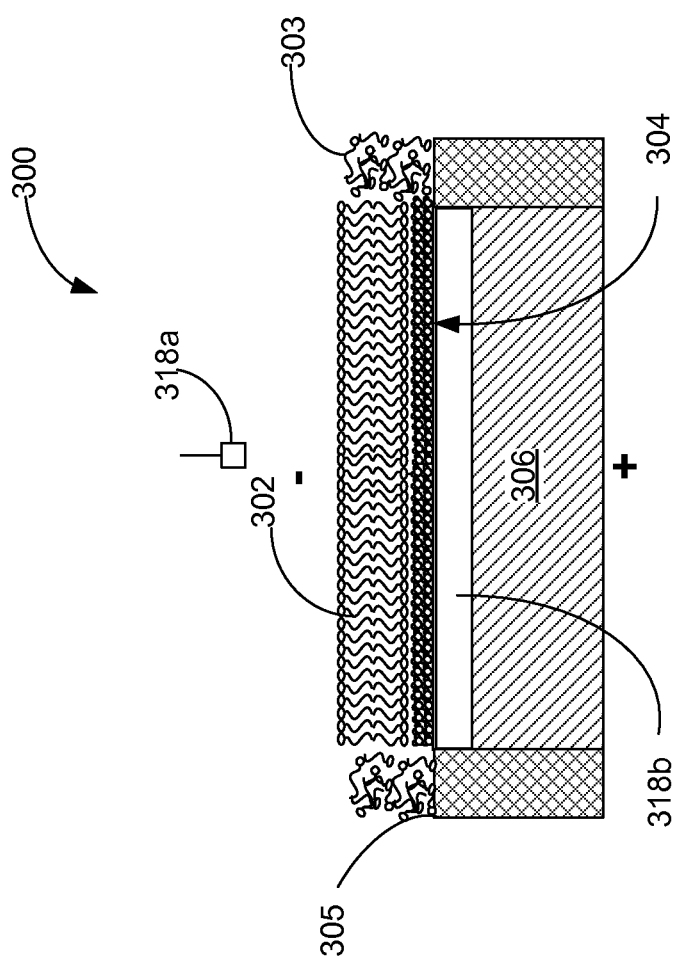
FIG. 4B is a diagram illustrating that nanopore device 300 is in a state in which a lipid bilayer 302 has been formed.
Figure 4C:
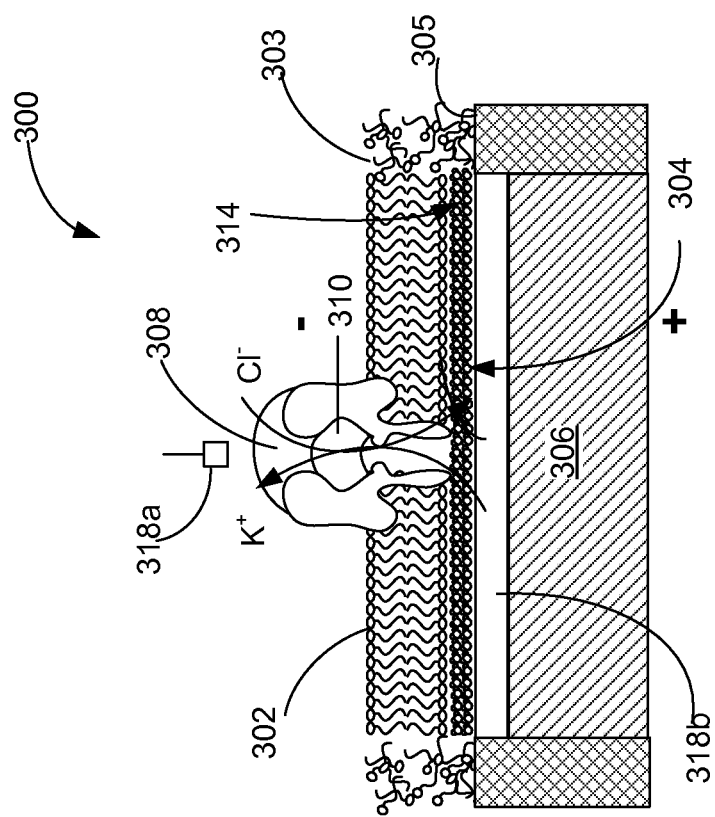
FIG. 4C is a diagram illustrating that nanopore device 300 is in a state in which a nanopore structure 308 with a nanopore 310 has been inserted into lipid bilayer 302.

FIGS. 4A-4C illustrate three different states of nanopore device 300. FIG. 4A is a diagram illustrating that nanopore device 300 is in a state in which a lipid bilayer has not yet been formed. FIG. 4B is a diagram illustrating that nanopore device 300 is in a state in which a lipid bilayer 302 has been formed. FIG. 4C is a diagram illustrating that nanopore device 300 is in a state in which a nanopore structure 308 with a nanopore 310 has been inserted into lipid bilayer 302.

Figure 5:
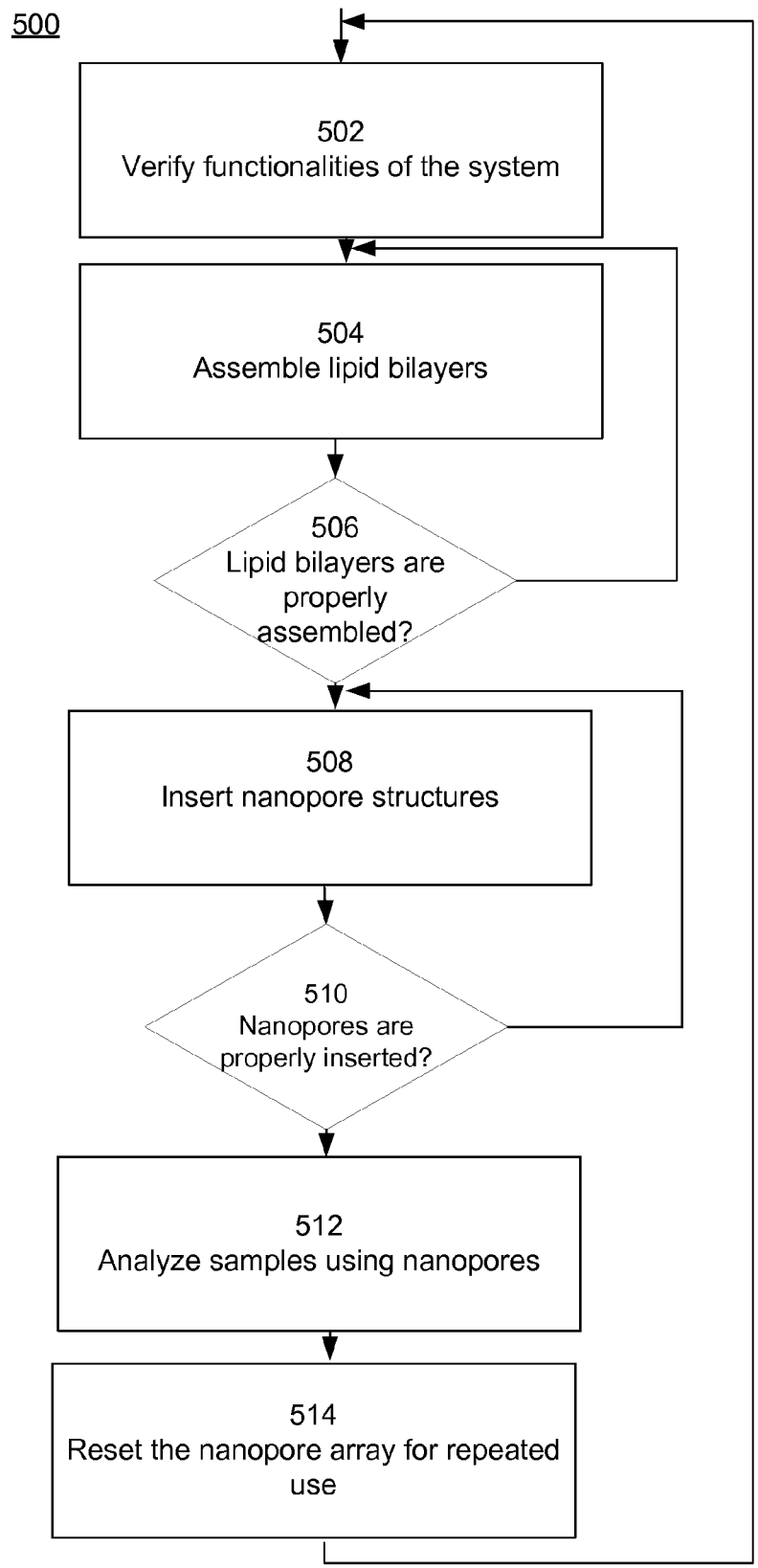
FIG. 5 is a flow diagram illustrating an embodiment of a process 500 for analyzing molecules using nanopore devices.

FIG. 5 is a flow diagram illustrating an embodiment of a process 500 for analyzing molecules using nanopore devices. In some embodiments, process 500 is a process that is performed by system 100 of FIG. 1.

At 502, various functionalities of system 100 are verified. In some embodiments, master controller 104 may send test signals to the modules of system 100, including nanopore array 102, temperature controller 106, and fluidic system 108. In response, each module may perform verification steps at the module. For example, nanopore array 102 may measure the current flowing in a particular nanopore device. After the verification steps are performed at the modules, each of the modules may send a response back to master controller 104 for verification purposes. Depending on the responses received from the various modules, master controller 104 may determine whether further verifications are needed. In some embodiments, the verification results may be stored in a log file. In some embodiments, if master controller 104 has detected any errors, then an alarm may be triggered or process 500 may be terminated.

In some embodiments, verification of the different modules may be performed at different levels, and the levels may be configurable. For example, master controller 104 may verify the functionalities of nanopore array 102 at the printed circuit board level or at the semiconductor chip level. In some embodiments, master controller 104 may verify the functionalities of a group of cells. If the number of cells within the group that are functioning properly falls below a certain threshold, then master controller 104 may determine that the group of cells is mal-functioning and that the group of cells should be disabled.

At 504, lipid bilayers are assembled. In some embodiments, master controller 104 may cause fluidic system 108 to deliver a lipid forming reagent to the cells of nanopore array 102. The lipid forming reagent is then deposited on lipid bilayer compatible surface 304 within a cell. As discussed above, the lipid bilayer may be formed using different materials, including different amphiphilic materials. Depending on the type of lipid bilayers to be formed, master controller 104 may cause different stimuli (e.g., electrical, temperature, chemical, or gas) to be applied to the cells to facilitate the assembling of the lipid bilayers.

At 506, it is determined whether the lipid bilayers are properly formed. Depending on the type of lipid bilayers to be formed, different physical or electrical property measurements (e.g., resistance, current, or capacitance measurements) may be made at the cells and then sent to master controller 104 via signal lines 114 for determining whether lipid bilayers are properly assembled. In some embodiments, steps 504 and 506 are repeated until master controller 104 has determined that lipid bilayers have been properly assembled in a minimum number of cells in nanopore array 102. In some embodiments, if the number of cells with lipid bilayers properly assembled falls below a certain threshold after a fixed period of time, master controller 104 may terminate process 500. In addition, an alarm may be triggered or an error message may be written to the log file. In some embodiments, if the number of cells with lipid bilayers properly assembled is above a certain threshold, master controller 104 may cause system 100 to proceed to step 508.

At 508, nanopore structures with nanopores are inserted. In some embodiments, master controller 104 may cause fluidic system 108 to deliver a nanopore forming reagent (e.g., a solution containing a-hemolysin) to the cells of nanopore array 102. Master controller 104 may cause different stimuli (e.g., electrical, temperature, chemical, or gas) to be applied to the cells to facilitate the insertion of the nanopore structures into the lipid bilayers.

At 510, it is determined whether the nanopore structures are properly formed. Depending on the type of nanopores to be formed, different measurements (e.g., resistance, current, or capacitance measurements) may be made at the cells and then sent to master controller 104 via signal lines 114 for determining whether nanopores are properly inserted. In some embodiments, steps 508 and 510 are repeated until master controller 104 has determined that nanopores have been properly inserted in a minimum number of cells in nanopore array 102. In some embodiments, if the number of cells with nanopores properly inserted falls below a certain threshold after a fixed period of time, master controller 104 may terminate process 500. In addition, an alarm may be triggered or an error message may be written to the log file. In some embodiments, if the number of cells with nanopores properly inserted is above a certain threshold, master controller 104 may cause system 100 to proceed to step 512.

At 512, samples are analyzed using the nanopores in nanopore array 102. In some embodiments, master controller 104 may cause fluidic system 108 to deliver samples to the sample chambers 316 in nanopore array 102. Depending on different factors, including the type of samples that are being analyzed and the type of nanopores formed, master controller 104 may cause different stimuli (e.g., electrical, temperature, chemical, or gas) to be applied to the cells to facilitate the manipulating, detecting, correlating, characterizing, analyzing and/or sequencing of molecules in the nanopores. Different measurements (e.g., resistance, current, or capacitance measurements) may be made at the cells and then sent to master controller 104 via signal lines 114. Master controller 104 may use the received measurements to detect, correlate, determine, characterize, sequence and/or discriminate various structural and chemical features of a molecule as the molecule stays inside the nanopore, traverses through the nanopore, or interacts with the nanopore.

At 514, nanopore array is reset and re-initialized for repeated uses. In some embodiments, nanopore array 102 may be reused multiple times. For example, nanopore array 102 may be used for analyzing different types of samples during different runs. In another example, nanopore array 102 may be reused for analyzing a single type of samples over multiple runs. New nanopores may be reformed in nanopore array 102 such that nanopore array 102 may be reused. New nanopores may be reformed in nanopore array 102 after the contents (e.g., lipid bilayers with nanopores inserted, lipid bilayers without nanopores inserted, and samples) in nanopore array 102 have been flushed out or rinsed out (e.g., using saline solution) by master controller 104 and fluidic system 108.

In some embodiments, master controller 104 may detect and determine whether there are any molecules or other contents of interest remaining in the cells of nanopore array 102. Master controller 104 and fluidic system 108 may selectively rinse out the contents (e.g., lipid bilayers) within cells in which no molecules or other contents of interest are found. The molecules or other contents of interest in the remaining cells may be retrieved. In one example, the molecules may be retrieved manually. In another example, master controller 104 and fluidic system 108 may deliver the molecules or other contents of interest to storage device 110 before the remaining contents are rinsed out. After 514, nanopore array 102 is ready for repeated uses again, and process 500 may be restarted at 502. In some embodiments, step 514 is performed before a nanopore array 102 is used for the first time. For example, nanopore array 102 is rinsed with saline solution before the functionalities of system 100 is checked at 502.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of analyzing molecules using a nanopore array including a plurality of cells included on a semiconductor chip, comprising:

causing one nanopore to be formed in a lipid bilayer formed in each of at least a portion of the plurality of the cells, comprising delivering a nanopore forming reagent by a fluidic system to the plurality of cells such that one nanopore may be formed in each of the at least a portion of the plurality of the cells, wherein the plurality of the cells comprises a thousand or more cells;

in each of the plurality of the cells: applying by a pair of electrodes and an electrical circuit a first electrical stimulus, wherein the first electrical stimulus is applied across a lipid bilayer if it has been formed in the particular cell, and sensing by the electrical circuit a first electrical measurement in response to the first electrical stimulus; and determining by a processor formation of one nanopore in each of at least a threshold number of cells based at least in part on the sensed first electrical measurements, wherein the threshold number of cells comprise a portion of the plurality of the cells, and in the event that formation of one nanopore in each of at least the threshold number of cells is not determined within a fixed period, terminating the method, and in the event that formation of one nanopore in each of at least the threshold number of cells is determined within the fixed period, begin causing the molecules to interact with the formed nanopores, comprising:

disabling the cells that have been determined as not having one formed nanopore, comprising disabling each of the disabled cells from drawing a current to the particular disabled cell and disabling any subsequent electrical stimulus from being applied to the particular disabled cell;

causing the molecules to interact with the formed nanopores in the cells that are not disabled, comprising delivering by the fluidic system a solution containing the molecules to the plurality of cells such that the molecules may interact with the formed nanopores;

in each of the cells that have been determined as having one formed nanopore: applying, by the pair of electrodes and the electrical circuit a second electrical stimulus, sensing by the electrical circuit a second electrical measurement in response to the second electrical stimulus, and determining a property of the molecules based at least in part on the second electrical measurement; and determining whether to begin to cause the nanopores to be reformed so that the cells with the reformed nanopores may be reused to interact with additional molecules.

2. The method of claim 1, wherein causing the molecules to interact with the formed nanopores in the cells that are not disabled comprises sending signals from a master controller to the chip.

3. The method of claim 1, wherein causing one nanopore to be formed in each of at least a portion of the plurality of the cells comprises:

causing lipid bilayers to be formed;

in each of the plurality of the cells, sensing by the electrical circuit a third electrical measurement; and determining whether to begin to cause the nanopores to be formed, wherein the nanopores are formed in at least a portion of the lipid bilayers.

4. The method of claim 3, wherein causing lipid bilayers to be formed comprises causing a lipid bilayer forming reagent to be deposited within the plurality of cells.

5. The method of claim 3, wherein determining whether to begin to cause the nanopores to be formed comprises determining by the processor formation of one lipid bilayer in each of at least a second threshold number of cells based at least in part on the sensed third electrical measurements.

6. The method of claim 1, further comprising determining a state for each cell.

7. The method of claim 6, wherein the state for each cell includes one of the following: a lipid bilayer is not formed, a lipid bilayer is formed, and a nanopore is formed.

8. The method of claim 6, wherein the determining of the state for each cell is based at least in part on a measurement received from the nanopore array.

9. The method of claim 1, further comprising:

determining that a particular cell is mal-functioning; and causing the cell to be disabled and at least some other cells to remain enabled.

10. The method of claim 1, further comprising causing a first stimulus to be applied to a first group of cells and causing a second stimulus to be applied to a second group of cells.

11. The method of claim 1, wherein causing the nanopores to be reformed so that the cells with the reformed nanopores may be reused to interact with additional molecules comprises:

causing a detection of any contents of interest in the cells; and in response to the detection of any contents of interest in the cells, causing the contents of interest to be flushed out of the cells by the fluidic system into a storage device prior to causing the nanopores to be reformed.

12. The method of claim 1, wherein causing the nanopores to be reformed comprises causing one or more cells to be rinsed.

13. The method of claim 1, further comprising causing a detection of any contents of interest in the cells.

14. The method of claim 13, further comprising causing the detected contents of interest to be extracted from the cells.

* * * * *

UNITED STATES PATENT AND TRADEMARK OFFICE
CERTIFICATE OF CORRECTION

| | |
|---|---|
| PATENT NO. | : 9,759,711 B2 |
| APPLICATION NO. | : 13/759701 |
| DATED | : September 12, 2017 |
| INVENTOR(S) | : Chen et al. |

It is certified that error appears in the above-identified patent and that said Letters Patent is hereby corrected as shown below:

In Item (56), Foreign Paten Documents, Page 3, Column 2, Line 42, patent document "WO 02/079519", date, delete "10/2012" and insert --10/2002--, therefor.

In Item (56), Other Publications, Page 4, Column 1, Line 11, delete "Clarke, et al. Continuous base identification for single-molucule nanpore DNA sequencing. Nat Nanotechnol. Apr. 2009;4(4):265-70. Epub Feb. 22, 2009." and insert --Clarke, et al. Continuous base identification for single-molecule nanopore DNA sequencing. Nat Nanotechnol. Apr. 2009;4(4):265-70. Epub Feb. 22, 2009.--, therefor.

In Item (56), Other Publications, Page 6, Column 2, Line 3, delete "Akeson, et al. Microsecond timescale discrimination among polycytidylic acid, polyadenylic acid, and plolyuridylic acid as homopolymers or a s segments within single RNA molecules. Biophys J. Dec. 1999; 77(6):3227-33." and insert --Akeson, et al. Microsecond time-scale discrimination among polycytidylic acid, polyadenylic acid, and polyuridylic acid as homopolymers or as segments within single RNA molecules. Biophys J. Dec. 1999; 77(6):3227-33.--, therefor.

In Item (56), Other Publications, Page 6, Column 2, Line 17, delete "Baaken, et al. Planar microelecrode-cavity array for hig-resolution and parallel electrical recording of membrane ionic currents. Lab Chip. Jun. 2008;8(6):938-44. Epub Apr. 16, 2008." and insert --Baaken, et al. Planar microelecrode-cavity array for high-resolution and parallel electrical recording of membrane ionic currents. Lab Chip. Jun. 2008;8(6):938-44. Epub Apr. 16, 2008.--, therefor.

In Item (56), Other Publications, Page 6, Column 2, Line 23, delete "Benner, et al. Sequence-specific detection of individual DNA polymerase complexes in real time using a nanopore. Nat Nanotechnol. Nov. 2007;2(11):718-24. Epub Oct. 28, 200." and insert --Benner, et al. Sequence-specific detection of individual DNA polymerase complexes in real time using a nanopore. Nat Nanotechnol. Nov. 2007;2(11):718-24. Epub Oct. 28, 2007--, therefor.

In Item (56), Other Publications, Page 6, Column 2, Line 55, delete "Mosquera et al., Thermal Decomposition and Fractal Properties of Sputter-Deposited Platinum Oxide Thin Films, Journal of of Signed and Sealed this
Seventeenth Day of April, 2018

Andrei Iancu
*Director of the United States Patent and Trademark Office*

Materials Research, pp. 829-836, Mar. 14, 2012." and insert --Mosquera et al., Thermal Decomposition and Fractal Properties of Sputter-Deposited Platinum Oxide Thin Films, Journal of Materials Research, pp. 829-836, Mar. 14, 2012--, therefor.

In Column 7, Line 50, delete "a-hemolysin" and insert --α-hemolysin--, therefor.